(12) United States Patent
Mitra et al.

(10) Patent No.: US 12,023,336 B2
(45) Date of Patent: Jul. 2, 2024

(54) ANTIVIRAL DRUG COMPOUNDS AND COMPOSITION THEREOF

(71) Applicant: NATIONAL CENTRE FOR CELL SCIENCE, Maharashtra (IN)

(72) Inventors: Debashis Mitra, Maharashtra (IN); Jay Trivedi, Maharashtra (IN)

(73) Assignee: NATIONAL CENTRE FOR CELL SCIENCE, Pune Maharashtra (IN)

( * ) Notice: Subject to any disclaimer, the term of this patent is extended or adjusted under 35 U.S.C. 154(b) by 899 days.

(21) Appl. No.: 17/055,321

(22) PCT Filed: May 10, 2019

(86) PCT No.: PCT/IN2019/050375
§ 371 (c)(1),
(2) Date: Nov. 13, 2020

(87) PCT Pub. No.: WO2019/220453
PCT Pub. Date: Nov. 21, 2019

(65) Prior Publication Data
US 2021/0196718 A1      Jul. 1, 2021

(30) Foreign Application Priority Data
May 15, 2018   (IN) .............................. 201821018105

(51) Int. Cl.
*A61K 31/519*   (2006.01)
*A61K 45/06*    (2006.01)
*A61P 31/18*    (2006.01)

(52) U.S. Cl.
CPC ............ *A61K 31/519* (2013.01); *A61K 45/06* (2013.01); *A61P 31/18* (2018.01)

(58) Field of Classification Search
CPC .................................................... A61K 31/519
USPC ......................................................... 514/249
See application file for complete search history.

(56) References Cited

U.S. PATENT DOCUMENTS 5,166,149 A     11/1992   Loev

FOREIGN PATENT DOCUMENTS

| WO | 93/18776 | 9/1993 |
|---|---|---|
| WO | 2005/016386 | 2/2005 |

*Primary Examiner* — Raymond J Henley, III
(74) *Attorney, Agent, or Firm* — Wenderoth, Lind & Ponack, L.L.P.

(57) ABSTRACT

The present invention relates to compounds and pharmaceutical composition having antiviral effects. Over 1200 molecules were screened and 55 molecules having statistically significant anti-HIV activity were identified and selected. The compound Methotrexate (MTX-HYD) and its analogues, the combinations thereof and their combination with other anti-retrovirals were selected for repurposing the compounds as anti-HIV drugs. The present invention may further relate to pharmaceutical composition comprising compounds in combination with active drugs having anti-HIV activity.

10 Claims, 13 Drawing Sheets

ANTIVIRAL DRUG COMPOUNDS AND COMPOSITION THEREOF

FIELD OF THE INVENTION

The invention described here relates to a field of pharmaceuticals and molecular biology. More specifically, the invention pertains to compounds and pharmaceutical composition having antiviral effects.

BACKGROUND OF THE INVENTION

Human immunodeficiency virus (HIV) is the causative agent of Acquired immunodeficiency syndrome (AIDS). Introduction of combination antiretroviral therapy (cART) has radically improved the management of HIV-1 infection and decreased both morbidity and mortality.

However, despite initial hopes to cure HIV, treatments were unable to fully eliminate the virus due to latent persistence of HIV in cells such as the central memory $CD4^+$ T-cells, hematopoietic stem cells, dendritic cells, and cells from the monocyte-macrophages lineage in the form of provirus. The large number of protease (PR), reverse transcriptase (RT), and integrase (IN) amino acid variants has implications for antiretroviral (ARV) therapy and presents a challenge to laboratories performing genotypic resistance testing.

Folic acid analogues are known to inhibit Dihydrofolate Reductase (DHFR) by competitively binding to the active site of the enzyme which ultimately inhibit DNA synthesis pathway in the cells. Trimethoprim, a folic acid analog may be used in combination sulfamethoxazole or dapsone for *pneumocystis* pneumonia in people with HIV/AIDS but this combination may cause some unwanted side effects. Therefore, pharmacokinetic drug interactions can significantly affect the efficacy and toxicity of chemotherapy.

Few prior arts disclose certain compounds that may be used against HIV infection. For instance, WO 1998037898 discloses analogues of folic acid in combination with para-aminobenzoic acid acting synergistically as anti-fungal agents. However, WO'898 fails to disclose that the combination may be used to inhibit DNA synthesis and act as an antiviral agent.

U.S. Pat. No. 8,470,822B2 pertains to use of folate mimetics and folate-receptor binding conjugates as the selective targeting of tumours expressing elevated levels of high-affinity folate receptors. However, US'822 fails to disclose that such compounds may inhibit DNA synthesis and may be used against severe viral infections.

The above cited prior art disclose folic acid analogues that may be used in treating fungal infections or tumor but not in viral infections. Selecting the right treatment strategies and combinations remain challenging in viral infections due to compatibilities among individual drugs and adherence, side-effects from long-term use of drugs and existence and emergence of drug-resistance profiles. Hence, an update or modification in the current approach is important to completely eradicate the viral infections.

OBJECT OF THE INVENTION

An object of the invention is to provide compounds and pharmaceutical composition having anti-HIV activity.

SUMMARY OF THE INVENTION

The present invention relates to compounds and pharmaceutical composition having antiviral effects. In particular the present invention pertains to compounds having anti-HIV activity.

More specifically, the present invention pertains Methotrexate, combinations thereof and compounds antiviral other with combination their analogues of methotrexate and pharmaceutical composition having anti-HIV activity. The present invention may further relate to pharmaceutical composition comprising compounds in combination with active drugs having anti-HIV activity.

DETAILED DESCRIPTION OF THE INVENTION

Figure 1:
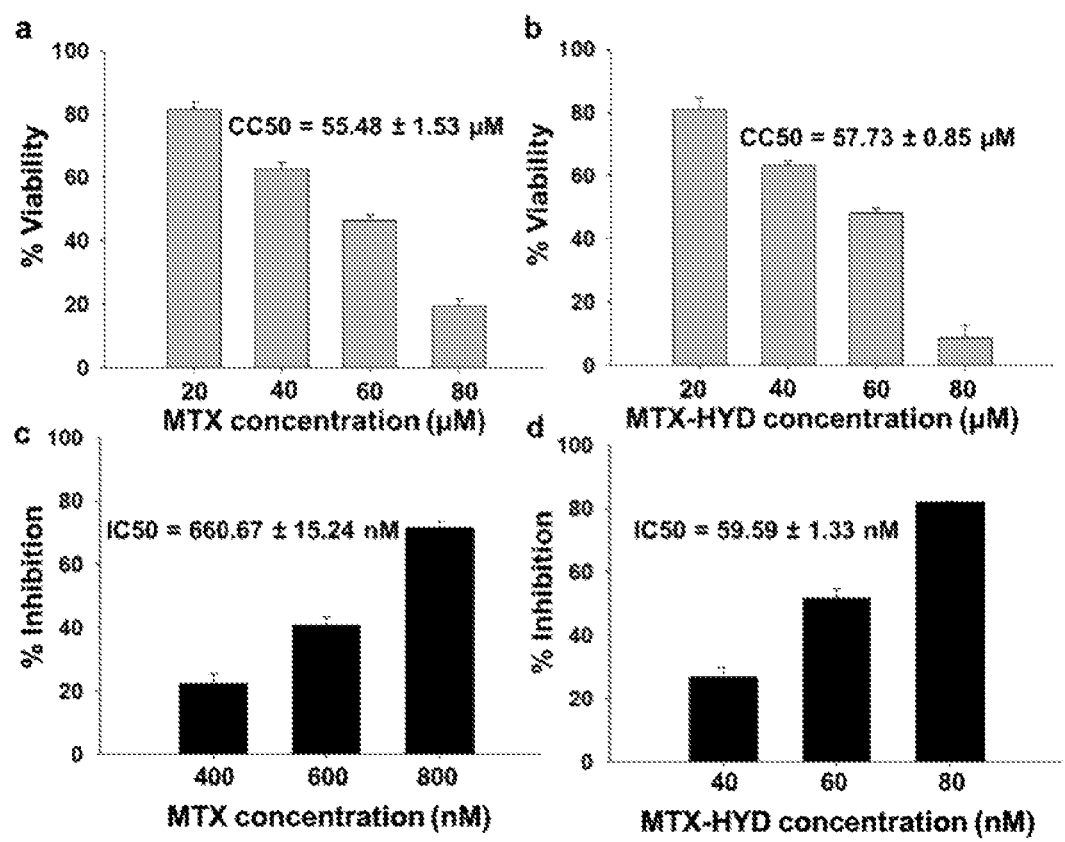
FIG. 1. depicts that Methotrexate-Hydrate (MTX-HYD) has approximately 10-fold better Therapeutic Index (TI) than Methotrexate (MTX). (a-b) CEM-GFP cells were treated with different concentrations of MTX-HYD and MTX and cytotoxicity was determined by MTT cell viability assay. Concentration at which cell viability was 50% was considered as $CC_{50}$ value. (c-d) CEM-GFP cells were infected with 0.5 MOI (Multiplicity of infection) of HIV-1NL4.3 virus in presence of MTX-HYD or MTX. 72-hours post infection supernatant was collected and virus production was determined by p24 antigen capture ELISA. Concentration at which virus production was inhibited 50% was considered as $IC_{50}$ value. Both $CC_{50}$ and $IC_{50}$ values were determined using SigmaPlot 12.5 (n=3).

The present invention is drawn to compounds that have anti-HIV activity. The compounds of the present invention are hitherto first reported for their anti-viral activity.

The present invention discloses the antiviral testing of around 1200 compounds, in precise 1280 compounds.

The present invention further discloses that 55 molecules are reported for the first time to have significant anti-viral activity. The molecules have antiviral activity at a statistically significant level and comprising an embodiment of the present invention is reported herein at Table 1 below.

TABLE 1

Compounds of the present invention inhibiting HIV-1$_{NL4.3}$ replication in TZM-bl cells

| Molecule Name | % Inhibition at 10 μM Concentration |
| --- | --- |
| Aurintricarboxylic acid | 97.17% |
| Tracazolate | 99.09% |
| Methotrexate Hydrate | 98.52% |
| Cyproterone acetate | 98.52% |
| Celecoxib | 95.09% |
| DL-alpha-Difluoromethylornithine hydrochloride | 97.06% |
| Dichloroisocoumarin | 97.06% |
| Doxazosin mesylate | 100% |
| SP600125 | 97.54% |
| BNTX maleate salt hydrate | 99.26% |
| MNS | 99.63% |
| Guanabenz acetate | 99.63% |
| 1,4-Bis[(p-hydroxyphenethyl)amino]-anthraquinone | 98.89% |
| Glipizide | 98.52% |
| Retinoic acid p-hydroxyanilide | 98.52% |
| GYKI 52466 hydrochloride | 99.26% |
| 6-Hydroxy-DL-DOPA | 96.67% |
| Kenpaullone | 98.71% |
| CP-154526 hydrochloride | 97.10% |
| S(+)-Isoproterenol (+)-bitartrate | 97.10% |
| NNC 55-0396 | 97.75% |
| RO 90-7501 | 99.67% |
| Indatraline hydrochloride | 97.43% |
| L-655,708 | 97.43% |
| MG 624 | 97.10% |
| Mitoxantrone | 97.10% |
| PD-407824 | 99.78% |
| Eprosartan mesylate | 99.78% |
| Nicardipine hydrochloride | 99.63% |
| NF 023 | 95.77% |
| Maprotiline hydrochloride | 98.94% |

TABLE 1-continued

Compounds of the present invention inhibiting HIV-1$_{NL4.3}$ replication in TZM-bl cells

| Molecule Name | % Inhibition at 10 µM Concentration |
|---|---|
| H-8 dihydrochloride | 99.57% |
| PMEG hydrate | 99.36% |
| Methoctramine tetrahydrochloride | 98.94% |
| PF-573228 | 97.23% |
| Nortriptyline hydrochloride | 99.15% |
| 6-Nitroso-1,2-benzopyrone | 99.15% |
| Sertraline hydrochloride | 99.36% |
| Topotecan hydrochloride hydrate | 98.06% |
| Perphenazine | 99.61% |
| Oxiracetam | 96.49% |
| Quinacrine dihydrochloride | 100% |
| PD173952 | 96.16% |
| S(−)-3PPP hydrochloride | 98.60% |
| (S)-Propranolol hydrochloride | 99.30% |
| K114 | 96.16% |
| (+)-Quisqualic acid | 99.30% |
| Auranofin | 96.08% |
| PD-166285 hydrate | 97.02% |
| SR 59230A oxalate | 97.52% |
| N-p-Tosyl-L-phenylalanine chloromethyl ketone | 98.76% |
| SC-51089 hydrate | 95.05% |
| BAY 61-3606 hydrochloride hydrate | 95.05% |
| Terfenadine | 98.71% |
| U0126 | 97.43% |

In an embodiment, the present invention is directed towards compounds having antiviral effects.

In particular, the compounds of the present invention discloses Methotrexate or analogue of Methotrexate (MTX) or Methotrexate and its analogues in combinations with other antivirals compounds for their use as antiviral agents.

The methotrexate of the present invention is selected from methotrexate-hydrate, Methotrexate dihydrate and Methotrexate tetrahydrate.

Figure 13:
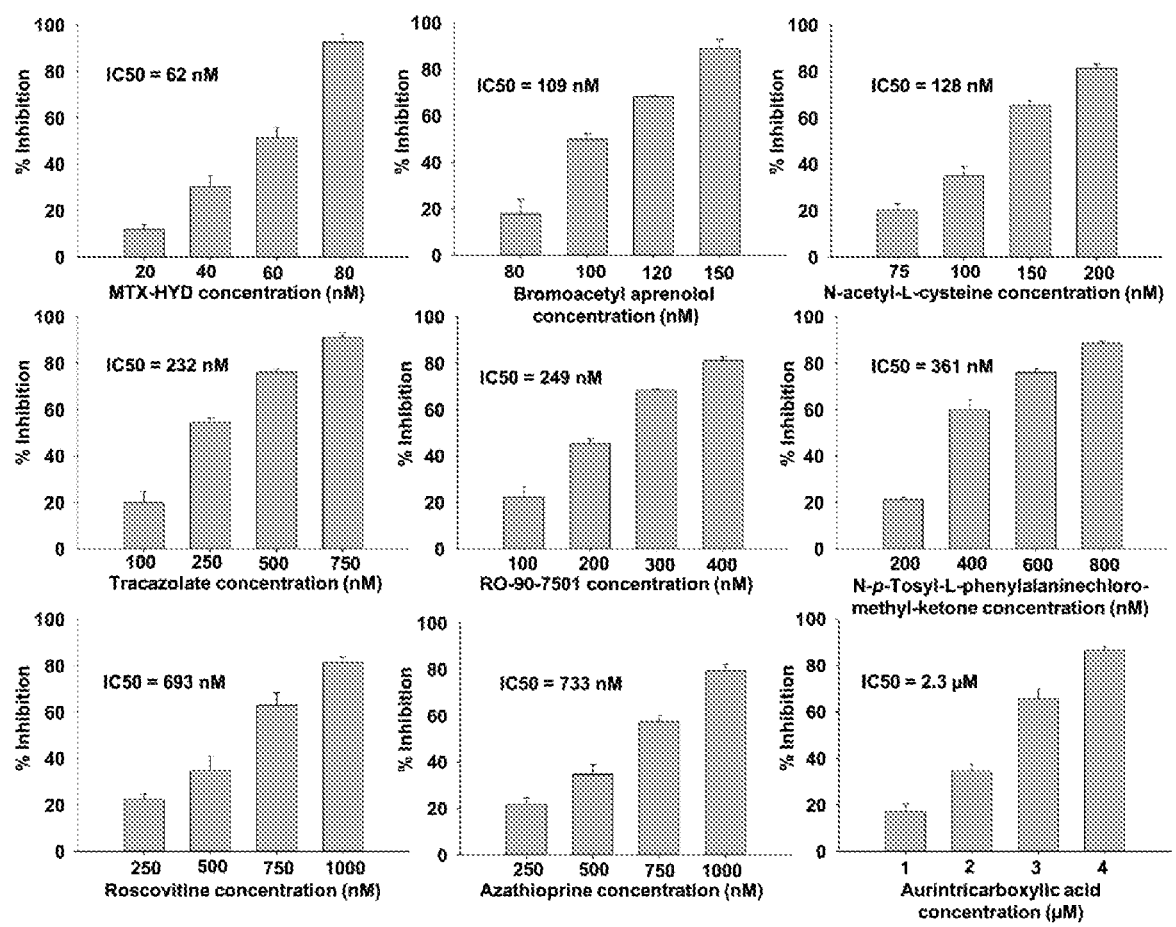
FIG. 13 depicts CEM-GFP cells were infected with 0.5 MOI of HIV-1NL4.3 and were treated with different concentrations of selected LOPAC[1280] at different concentrations. Untreated cells were considered as infected controls and DMSO treated cells were considered as vehicle controls. 72-hours post infection, supernatant was collected and virus production was determined by p24 antigen capture ELISA. Concentration at which virus production was inhibited 50% was considered as $IC_{50}$ which was determined using Sigma Plot 12.5 (n=3).

In total, 9 molecules were further tested in T-cell line, CEM-GFP by determining their IC$_{50}$ value. The MTX-HYD of present invention was selected based on the lowest IC$_{50}$ value out of 9 molecules tested (FIG. 13).

MTX-HYD has ~10 fold better anti-HIV potential than MTX (FIG. 1).

Figure 2:
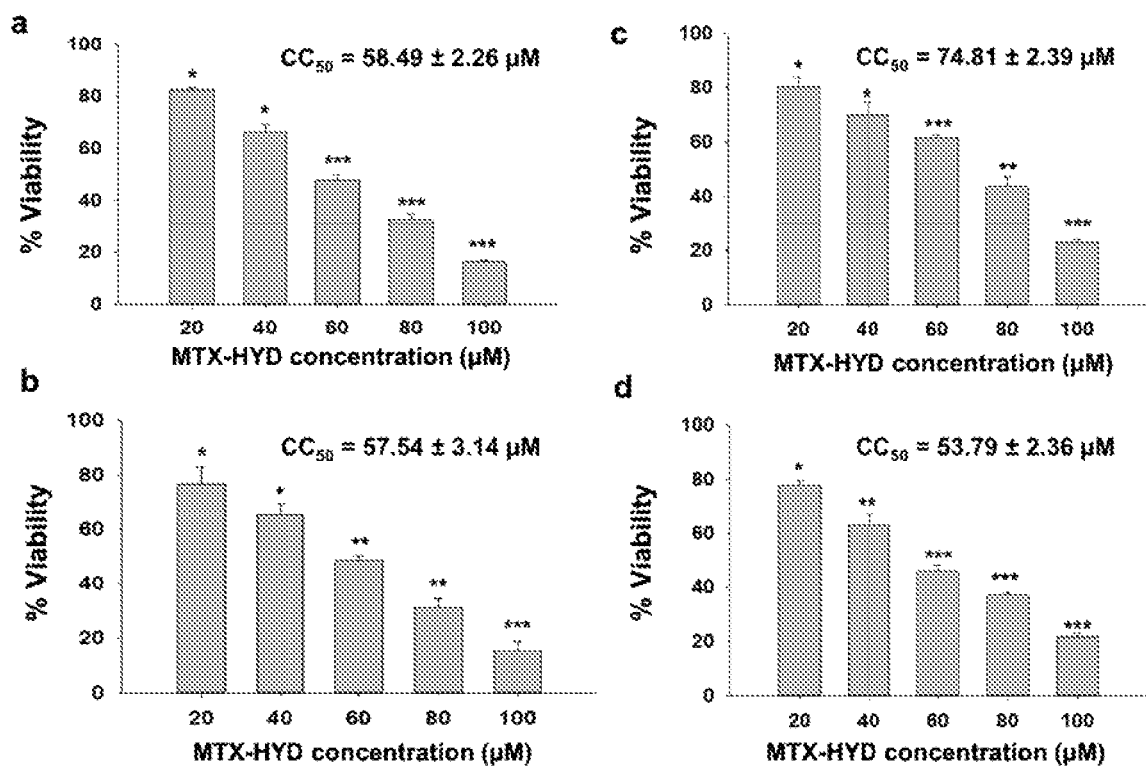
FIG. 2. depicts that MTX-HYD has similar cytotoxicity profile in different cell types. (a) CEM-GFP, (b) Jurkat J6, (c) U937 and (d) hPBMCs were treated at different concentrations of MTX-HYD. Untreated and DMSO treated cells were taken as controls. Concentration at which cell viability was 50% was considered as $CC_{50}$ value which was determined using SigmaPlot 12.5 (n=3).
Figure 3:
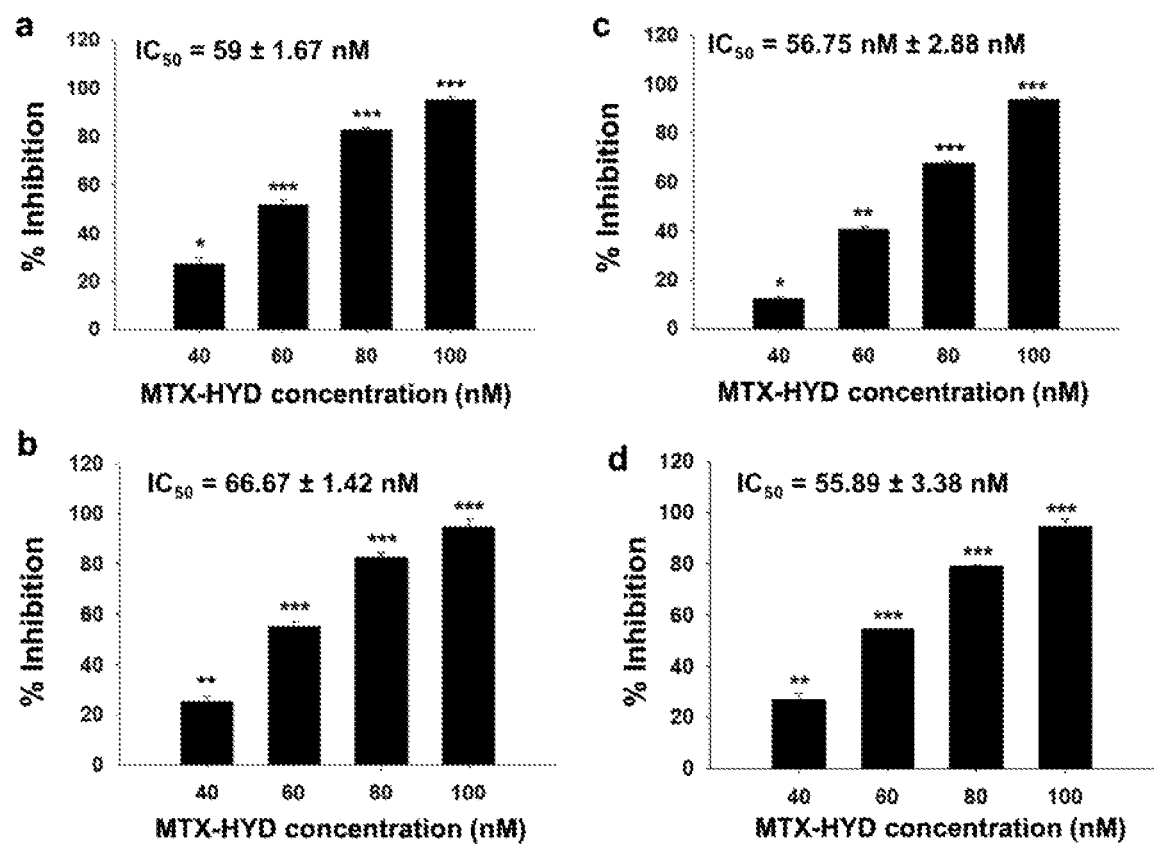
FIG. 3. depicts that MTX-HYD inhibits HIV-1 replication at significantly low concentration. $IC_{50}$ value of MTX-HYD was determined in (a) CEM-GFP, (b) Jurkat J6, (c) U937 and (d) hPBMCs infected with 0.5 MOI of HIV-1NL4.3 by measuring virus production in supernatant by p24 antigen capture ELISA. Concentration at which virus production was inhibited 50% was considered as $IC_{50}$ value which was determined using SigmaPlot 12.5 (n=3).

MTX-HYD shows similar cytotoxicity profile in all the cell types tested with CC$_{50}$ value ranging from 50 µM to 75 µM (FIG. 2). Further, the anti-HIV activity of MTX-HYD is cell-type independent phenomena and it possess significant Therapeutic Index in T-cell lines (CEM-GFP and Jurkat J6), Monocytic cell line (U937) and primary cells (hPBMCs) (FIG. 3).

Figure 4:
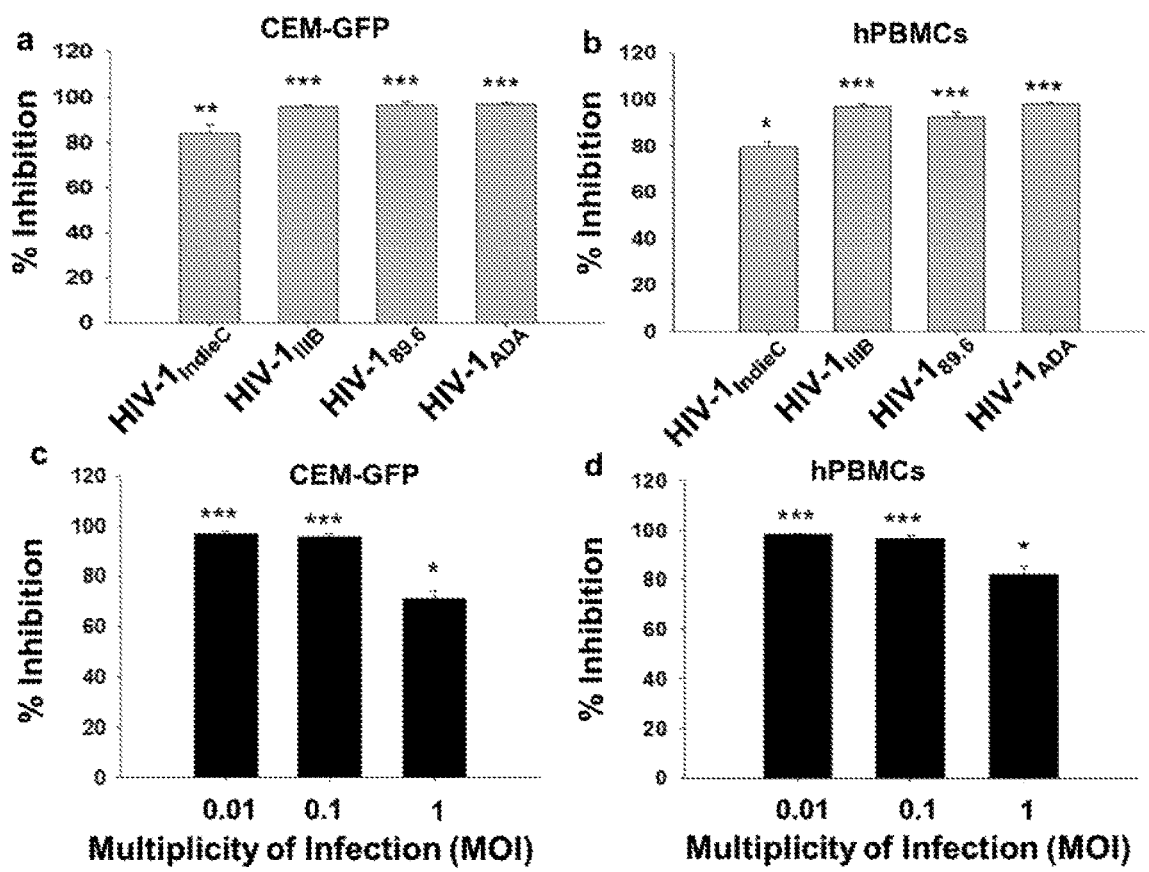
FIG. 4. depicts anti-HIV activity of MTX-HYD is not virus isolate and viral load dependent phenomena. (a) CEM-GFP cells and (b) hPBMCs were infected with 0.5 MOI of different isolates of HIV-1 and supernatant was collected 72-hours post infection. Virus production in supernatant was measured by p24 antigen capture ELISA. (c) CEM-GFP cells and (d) hPBMCs were infected with 0.01, 0.1 and 1 MOI of HIV-1NL4.3. Supernatant was collected at different time points of infection and virus production was determined by p24 antigen capture ELISA (n=3).

MTX-HYD may possess highly conserved anti-HIV activity and may inhibit HIV-1 replication in virus isolate and viral load independent manner (FIG. 4).

Figure 5:
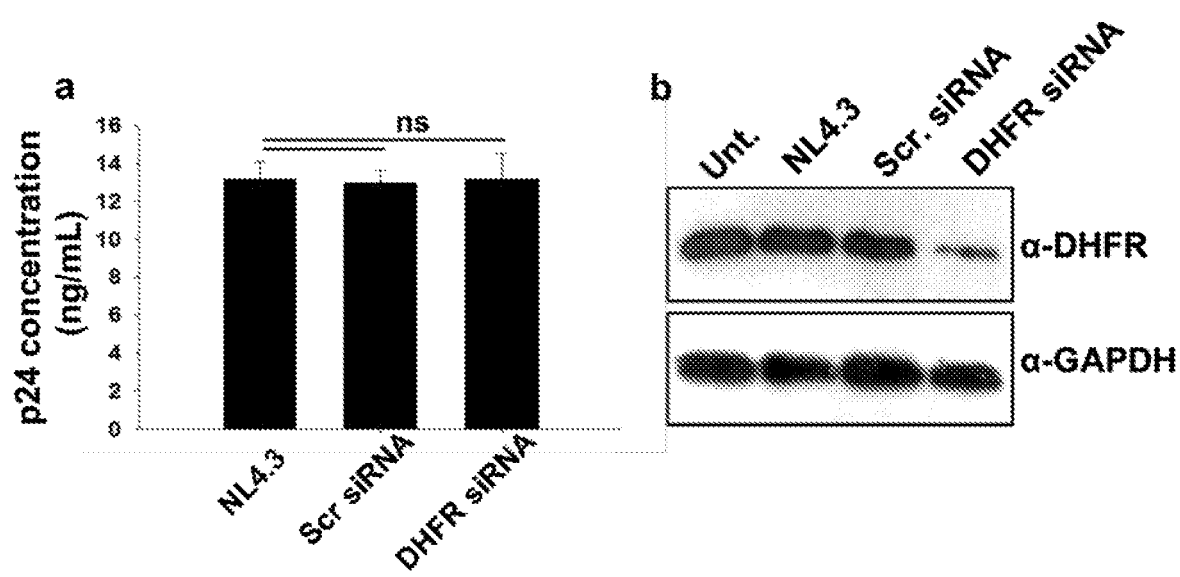
FIG. 5. depicts that DHFR does not play a significant role in HIV-1 life cycle. (a) CEM-GFP cells were transfected with DHFR siRNA (150 nM). 24-hour post transfection, cells were infected with 0.5 MOI of HIV-1NL4.3. Virus production in supernatant was determined 72-hour post infection by p24 antigen capture ELISA. (b) immunoblotting for analysing silencing of DHFR. (Unt.=Untransfected/Uninfected), (NL4.3=HIV-$1_{NL4.3}$ infected/untransfected) (n=3).

DHFR, the well-established target of MTX-HYD may not play a vital role in HIV-1 life cycle (FIG. 5).

Figure 6:
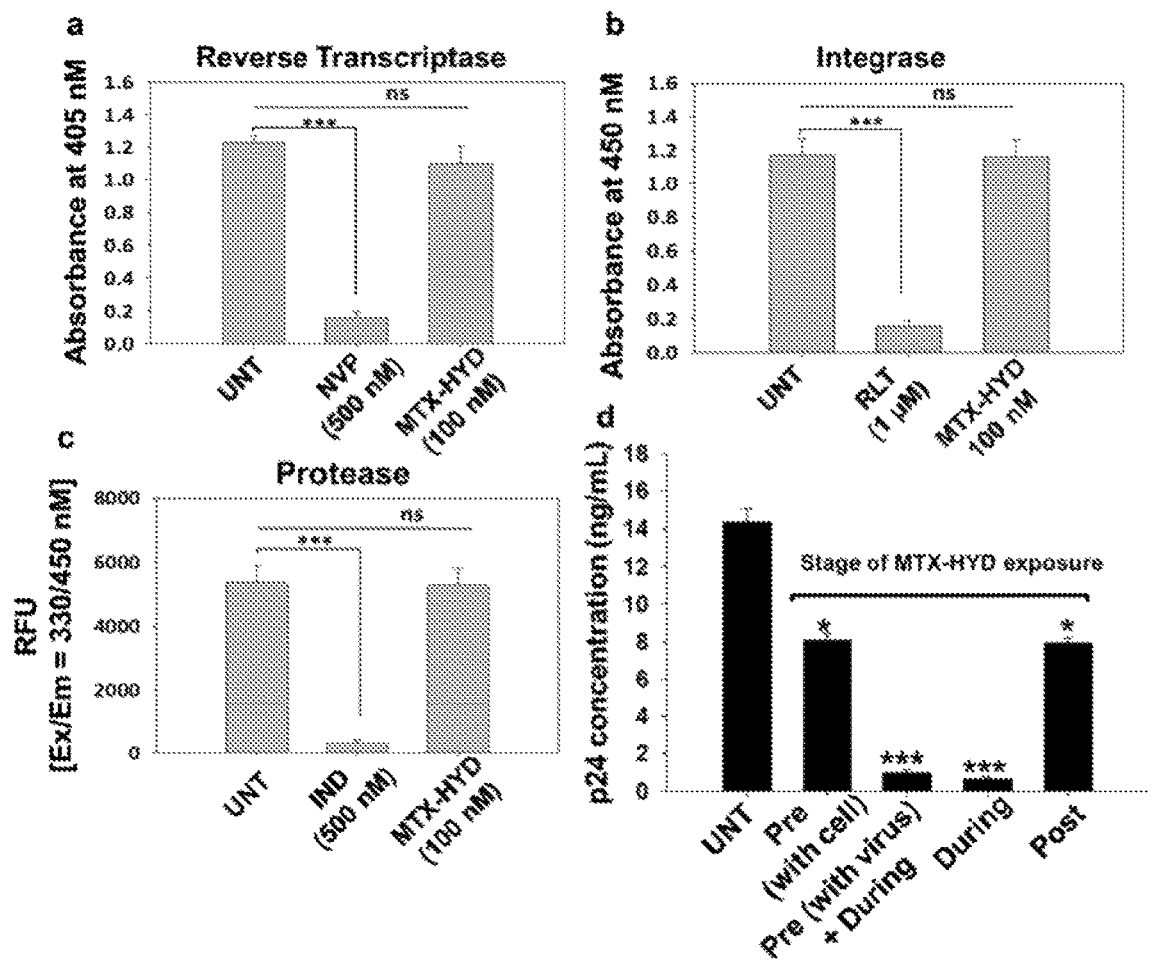
FIG. 6. depicts that MTX-HYD does not target viral enzymes and works at an early stage of the life cycle. MTX-HYD (100 nM) was tested on viral enzymes Reverse Transcriptase (a), Integrase (b) and Protease (c) in an in vitro cell free assay system. Nevirapine (NVP) (500 nM), Raltegravir (RLT) (1 μM), and Indinavir (IND) (500 nM) were used as the control inhibitors of RT, IN, and PR respectively. Untreated wells (UNT) were considered as negative controls. (d) CEM-GFP cells were infected with 0.5 MOI of HIV-1NL4.3 and treated with MTX-HYD (100 nM) at different stages of virus infection. 72-hours post-infection virus production was determined in supernatant by p24 antigen capture ELISA (n=3).

MTX-HYD may not inhibit the viral enzymes Reverse transcriptase, Integrase and Protease (FIG. 6 a-c) and may inhibit HIV-1$_{NL4.3}$ replication at early stages of virus life cycle (FIG. 6 d).

Figure 7:
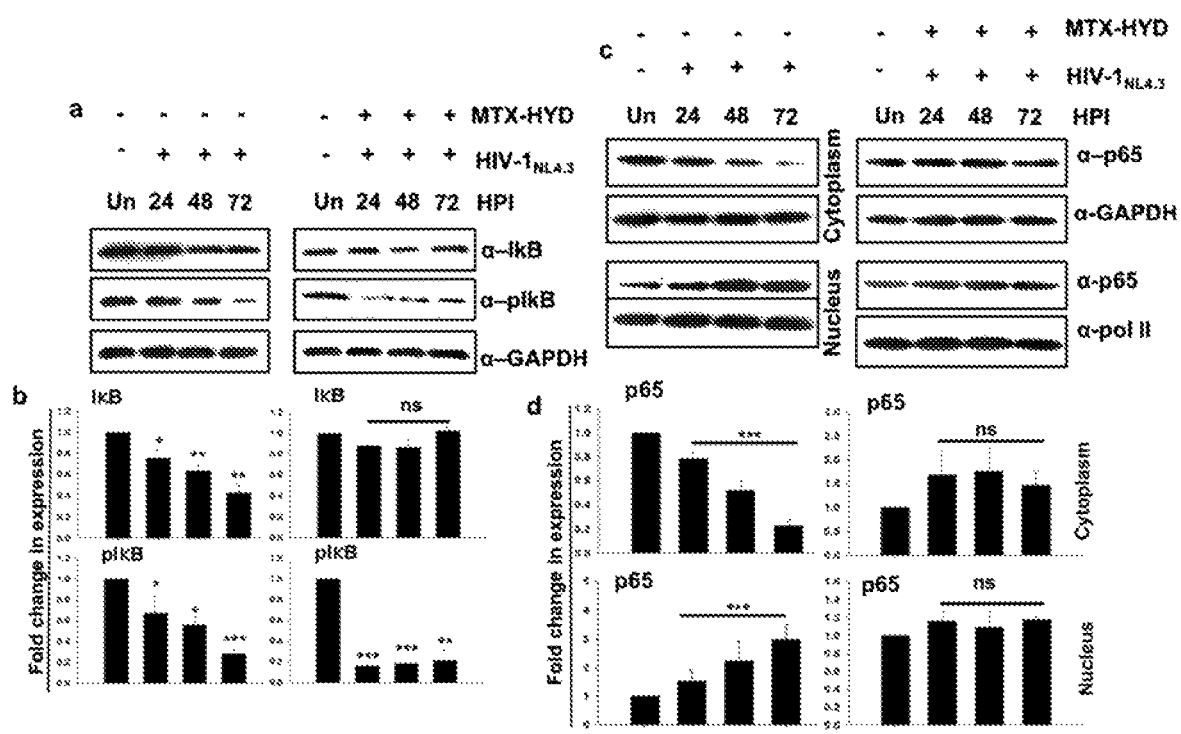
FIG. 7. depicts that MTX-HYD inhibits NF-xB pathway. (a) CEM-GFP cells were infected with 0.5 MOI of HIV-1NL4.3 in presence or absence of MTX-HYD (100 nM). Cells were harvested at different time points (24 h, 48 h and 72 h) post-infection. Phosphorylation of IxB was analysed by immunoblotting. (c) CEM-GFP cells were infected with 0.5MOI of HIV-1$_{NL4.3}$ in presence or absence of MTX-HYD (100 nM) and nuclear cytoplasmic fractions were prepared using NE-PER nuclear-cytoplasmic fractionation kit. p65 levels in both cytoplasm and nucleus were analyzed by immunoblotting. (b and d) Densitometric analysis of immunoblots using QuantityOne software (n=3).

Mechanistically, MTX-HYD may inhibit IkB phosphorylation which in turn may inhibit NF-kB p65 activation and nuclear localization (FIG. 7).

Figure 9:
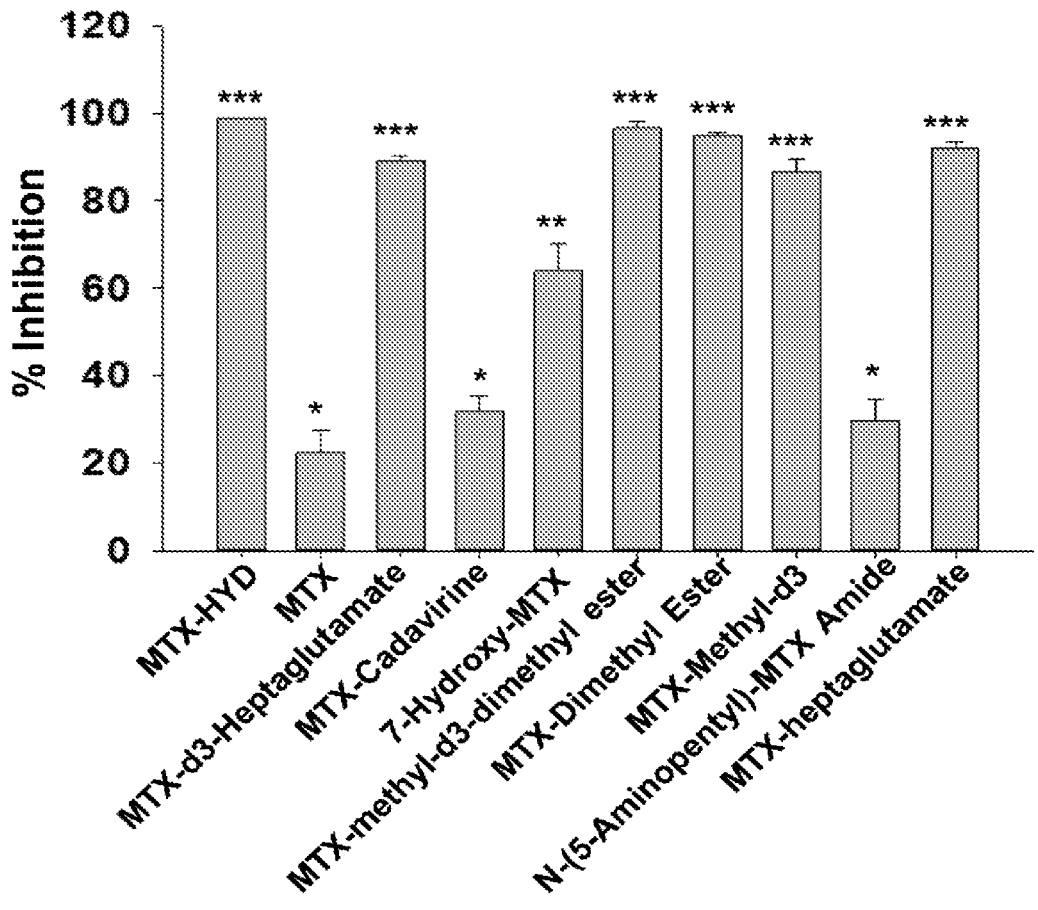
FIG. 9. depicts that MTX analogues inhibit HIV-1 replication with different efficiency. CEM-GFP cells were infected with 0.5 MOI of HIV-1NL4.3 and treated with different analogues of MTX at 100 nM concentration. MTX-HYD and original MTX were also considered in the experiment for the comparison purpose. 72-hours post infection, supernatant was collected and virus production was determined by p24 antigen capture ELISA.

The Methotrexate analogue may be selected from group comprising MTX-methyl-d3-Dimethyl Ester, MTX Dimethyl Ester, MTX-methyl-d3, MTX heptaglutamate and MTX-d3 heptaglutamate, preferably, MTX-methyl-d3-Dimethyl Ester, MTX-Dimethyl Ester and MTX-methyl-d3 (FIG. 9).

The analogues-mediated inhibition of virus may be performed in vitro on various virus isolates such as HIV-1$_{NL4.3}$, HIV-1$_{IndieC}$, HIV-1$_{IIIB}$, HIV-1$_{ADA}$, HIV-1$_{89.6}$. Preferably, the analogues may inhibit the replication of all HIV-1 isolates tested with high efficiency.

The antiviral activity of the analogues in terms of efficacy may be tested in dose dependent manner by determining the Therapeutic Index (TI), performing MTT cell proliferation assay, HIV-1 infection and anti-HIV activity assay, ELISA for calculating the percentage inhibition of virus production, RNA dependent DNA polymerase activity assay of HIV-1 RT (RDDP Assay), Cell free assay for HIV-1 Integrase activity and cell free assay for HIV-1 Protease activity, anti-HIV activity on various cell lines such as Jurkat J6 (CD4+T cell line), TZM-bl cell line, CEM-GFP, U937 cell-lines and primary cells (hPBMCs) to monitor HIV infection and effect of the compounds on inhibition of virus production.

The in vitro efficacy of the MTX-analogues may be based upon the CC$_{50}$ values (concentrations of drug required to reduce cell viability by 50%) and IC$_{50}$ values (concentration of the drug required to inhibit 50% viral replication). The relative effectiveness of the analogues in inhibiting viral replication compared to inducing cell death may be indicated by the ratio of CC$_{50}$ values to IC$_{50}$ values as the therapeutic index of the MTX analogues. The activity of the methotrexate analogues of the present invention are provided herein below at Table 2.

TABLE 2

Therapeutic index [TI = CC$_{50}$/IC$_{50}$] of selected MTX analogues in CEM-GFP cells.

| MTX Analogues | CC50 | IC50 | TI |
|---|---|---|---|
| MTX-methyl-d3-Dimethyl Ester | 47.34 ± 1.51 | 9.9 ± 1.51 | 4781.81 |
| MTX Dimethyl Ester | 54.33 ± 3.78 | 32.43 ± 0.87 | 1675.3 |
| MTX-methyl-d3 | 46.44 ± 1.08 | 42.07 ± 3.84 | 1103.87 |
| MTX heptaglutamate | 39.92 ± 1.00 | 73.67 ± 1.65 | 541.87 |
| MTX-d3 heptaglutamate | 40.48 ± 3.43 | 77.85 ± 2.42 | 519.97 |

The above Table 2 represents the Therapeutic Index (TI) of MTX analogues which may inhibit HIV-1$_{NL4.3}$ replication >95% at 100 nM concentration in CEM-GFP cells. The analogues such as MTX-methyl-d3-dimethyl ester, MTX dimethyl ester and MTX methyl-d3 may have higher therapeutic index than MTX-HYD (FIGS. 1 to 3).

The analogues such as MTX-methyl-d3-dimethyl ester, MTX dimethyl ester and MTX methyl-d3 inhibits replication of HIV-1$_{NL4.3}$ (FIG. 9).

Figure 10:
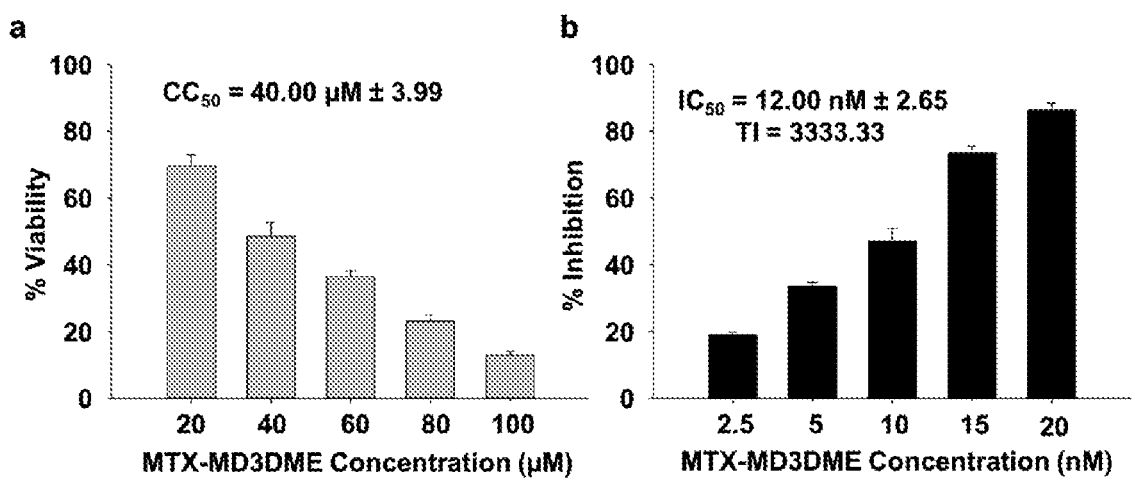
FIG. 10. depicts that Methotrexate-methyl-d3-Dimethyl ester (MTX-MD3DME) has significantly high therapeutic index (TI) in hPBMCs. (a) hPBMCs were treated with different concentration of Methotrexate-methyl-d3-Dimethyl ester (MTX-MD3DME) and cytotoxicity was determined by MTT cell viability assay. Concentration at which cell viability was 50% was considered as $CC_{50}$ value. (b) hPBMCs were infected with 0.5 MOI of HIV-1NL4.3 in presence or absence of Methotrexate-methyl-d3-Dimethyl ester (MTX-MD3DME). 72-hours post infection supernatant was collected and virus production was determined by p24 antigen capture ELISA. Concentration at which the virus production was inhibited by 50% was considered as $IC_{50}$ value. Both $CC_{50}$ and $IC_{50}$ values were determined using SigmaPlot 12.5 (n=3).
Figure 11:
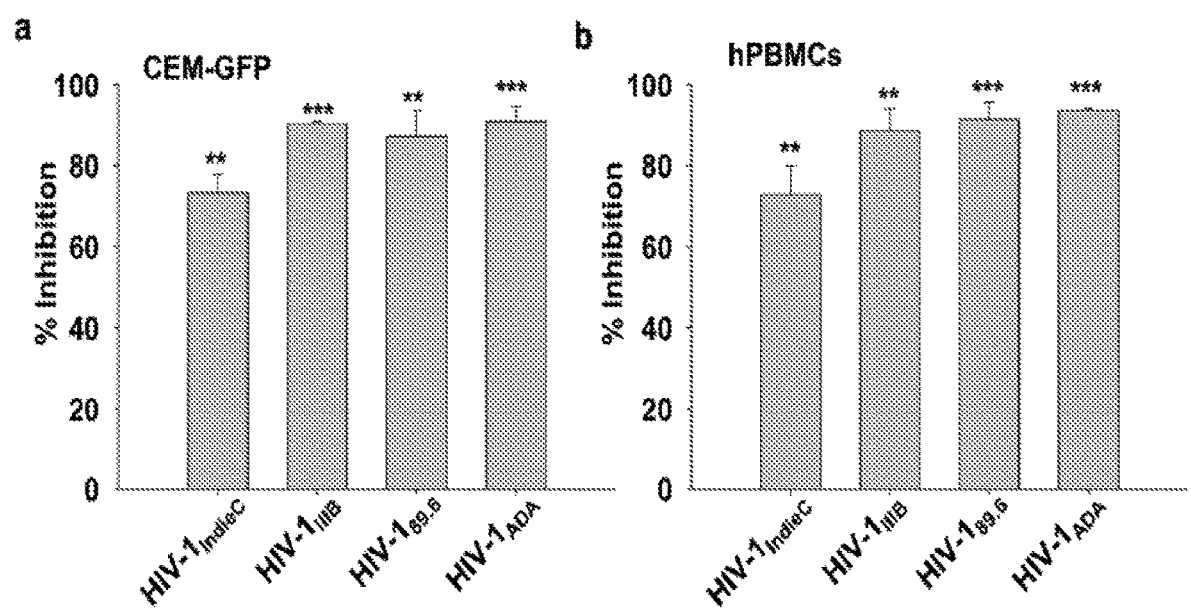
FIG. 11. depicts that anti-HIV activity of Methotrexate-methyl-d3-Dimethyl ester (MTX-MD3DME) is not virus isolate specific phenomena. (a) CEM-GFP cells and (b) hPBMCs were infected with 0.5 MOI of different isolates of HIV-1 in presence or absence of Methotrexate-methyl-d3-Dimethyl ester (MTX-MD3DME) (25 nM). 72-hours post infection supernatant was collected and virus production was determined by p24 antigen capture ELISA (n=3).

MTX-methyl-d3-dimethyl ester may inhibit HIV-1$_{NL4.3}$ replication with high efficiency in primary cells (hPBMCs) (FIG. 10) and may also inhibit other virus isolates such as HIV-1$_{IndieC}$, HIV-1$_{IIIB}$, HIV-1$_{ADA}$, HIV-1$_{89.6}$ with higher Therapeutic Index (TI) than Methotrexate Hydrate (MTX-HYD) both in CEM-GFP and hPBMCs (FIG. 11).

Figure 8:
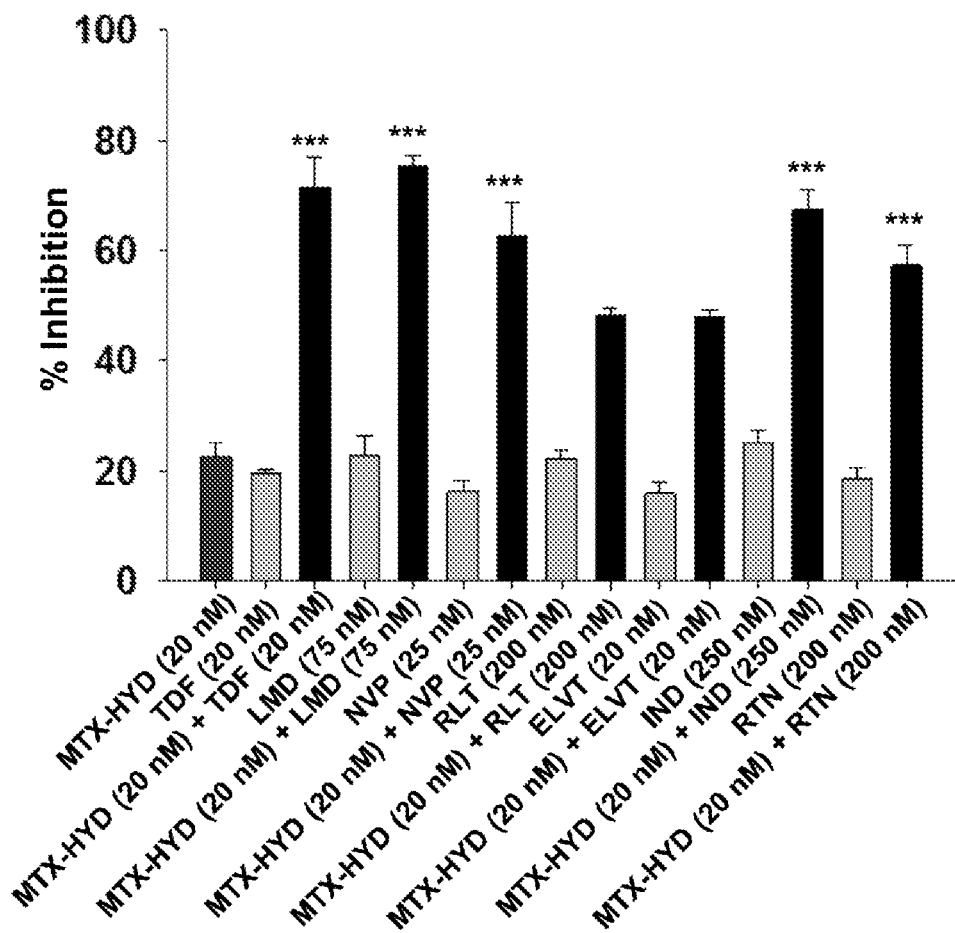
FIG. 8. depicts that combination of MTX-HYD with selected ART drugs including RT and PR inhibitors results in significant synergistic anti-HIV activity. Whereas, combination of MTX-HYD with IN inhibitors shows additive effect. CEM-GFP cells were infected with 0.5 MOI of HIV-1NL4.3. Cells were treated with MTX-HYD (20 nM) (dark grey bar) and also with known HAART drugs including TDF (20 nM), LMD (75 nM), NVP (25 nM), RLT (200 nM), ELVT (20 nM), IND (250 nM), RTN (200 nM) individually (light grey bars) or in combination with MTX-HYD (black bars). Untreated cells were taken as negative control whereas DMSO treated cells were taken as vehicle control. Virus production was determined in supernatant by p24 antigen capture ELISA, 72-hours post infection.
Figure 12:
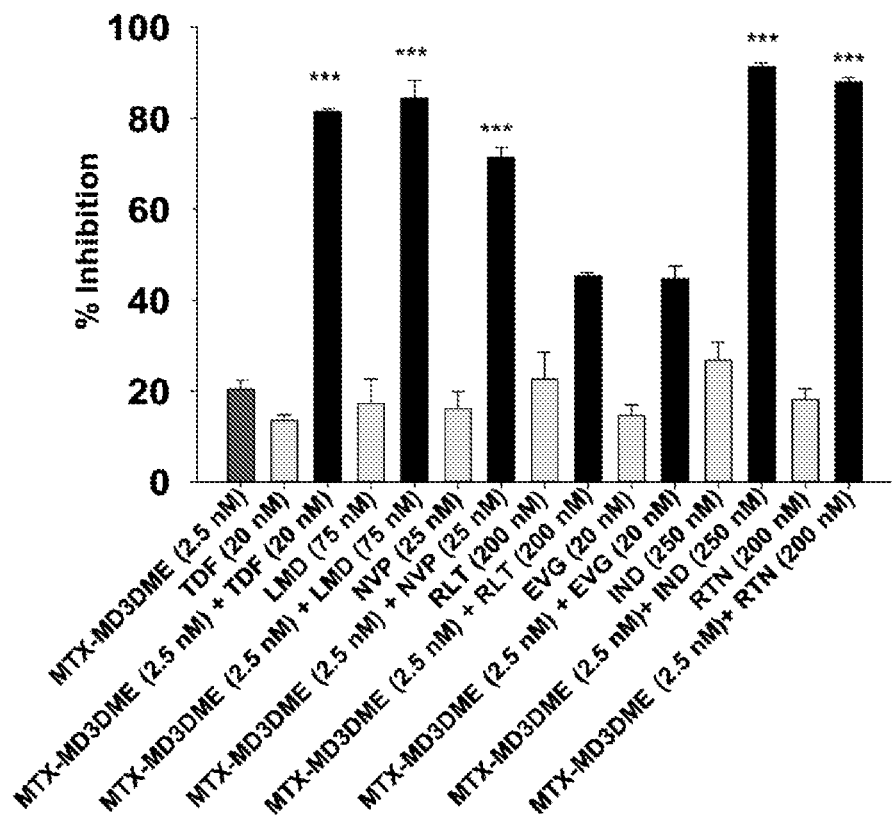
FIG. 12. Depicts that combination of Methotrexate-methyl-d3-Dimethyl ester (MTX-MD3DME) with known ART candidates including RT and PR inhibitors results in significant synergistic anti-HIV activity. CEM-GFP cells were infected with 0.5 MOI of HIV-1NL4.3. Cells were treated with Methotrexate-methyl-d3-Dimethyl ester (MTX-MD3DME) (2.5 nM) (dark grey bar) and also with known ART candidates including TDF (20 nM), LMD (75 nM), NVP (25 nM), RLT (200 nM), ELVT (20 nM), IND (250 nM), RTN (200 nM) individually (light grey bars) or in combination with MTX-HYD (black bars). Untreated cells were taken as negative control whereas DMSO treated cells were taken as vehicle control. Virus production was determined in supernatant by p24 antigen capture ELISA, 72-hours post infection (n=3).

In another embodiment, the pharmaceutical composition of the present invention may comprise analogues of methotrexate and at least one active drugs having anti-HIV activity. In other words, the Methotrexate-Hydrate (FIG. 8) and its analogues (FIG. 12) may be used in combination with other antiviral compounds as synergistic combinations for anti-viral therapy.

The other anti-viral compounds that may be administered in addition to MTX-HYD or MTX analogues may be selected from the group comprising Tenofovir (TDF), Indinavir (IND), Raltegravir (RLT) and Maraviroc (MRV), Lamivudine (LMD), Nevirapine (NVP), Elvitegravir (EVG) and Ritonavir (RTN).

The present invention discloses Methotrexate and its analogue where the Methotrexate and its analogues are used in combination with other antiviral compounds as antiviral agents.

The present invention discloses Anti-viral compounds. The antiviral compounds may be selected from group comprising Tenofovir (TDF), Indinavir (IND), Raltegravir (RLT) and Maraviroc (MRV), Lamivudine (LMD), Nevirapine (NVP), Elvitegravir (EVG) and Ritonavir (RTN).

The present invention discloses Methotrexate and its analogue where the antiviral activity is performed in vitro on virus isolates such as HIV-1$_{NL4.3}$, HIV-1$_{IndieC}$, HIV-1$_{IIIB}$, HIV-1$_{ADA}$, HIV-1$_{89.6}$ with high efficiency.

The present invention discloses Methotrexate and its analogue where the dose to obtain the antiviral activity may be in the range of 0.01 mg/kg body weight to 100 mg/kg body weight, preferably 0.01 mg/kg body weight to 75 mg/kg body weight, and most preferably 0.01 mg/kg body weight to 50 mg/kg body weight.

The present invention discloses a pharmaceutical composition comprising Methotrexate or its analogue in combination with other antivirals as claimed in claim 1, along with pharmaceutically acceptable excipients.

The present invention discloses pharmaceutical composition where the pharmaceutical composition is administered as oral, intradermal, transdermal, parenteral, intramuscular, intrathecal and suppository.

Advantages

The analogues of the present invention may act on the early stages of virus cycle.
The analogues of the present invention seem to have potential in studying the HIV infections.
The analogues may have significant effect on more than one strain of HIV in vitro.
The analogues have proven efficacy over other known compounds against HIV infection.

EXAMPLES

The following examples are given by the way of illustration of the present invention and therefore should not be construed to limit the scope of the present invention.

Example 1. Cell Culture

HEK-293T (Human Embryonic Kidney Fibroblast) and Jurkat J6 (CD4+T cell line) cell-lines were obtained from NCCS Cell Repository, NCCS, Pune, India. The HeLa based reporter cell line TZM-bl was initially generated from parental JC.53 cells which contains two separate copies of Luciferase and β-Galactosidase downstream to HIV-1 5' Long Terminal Repeat (LTR) promoter. CEM-GFP, a reporter CD4$^+$ T cell line contains GFP gene downstream to 5' LTR promoter. Both TZM-bl and CEM-GFP were obtained from NIH AIDS Reagent Program, Division of AIDS, NIH. CEM-GFP, Jurkat J6 and U937 cell-lines were grown in RPMI-1640 medium (Invitrogen, USA) and HEK-293T and TZM-bl cells were grown in DMEM medium both containing 10% fetal bovine serum (FBS) in presence of 100 U/ml of penicillin (Invitrogen, USA) and 100 µg/ml streptomycin (Invitrogen, USA) to avoid bacterial contamination. 500 µg/ml G418 (Invitrogen, USA) was added to the media containing CEM-GFP cells as a selective antibiotic.

Example 2. Isolation of Human Peripheral Blood Mononuclear Cells (hPBMCs)

Blood of seronegative donors was obtained from Indian Serological Institute (ISI) Blood bank, Navi Peth, Pune. hPBMCs were isolated from the blood using Histopaque 1077 by gradient centrifugation as described previously. Briefly, blood was diluted using serum free RPMI-1640. Diluted blood was then carefully layered on top of Histopaque 1077 without disturbing the gradient. PBMCs were separated by centrifugation at 1800 rpm for 25 minutes. PBMCs were then collected and washed twice with serum free RPMI and seeded at the density of 10$^6$ cells/mL of media and activated with PHA and used for further experiments (FIG. 4).

Example 3. MTT Cell Proliferation Assay

Cytotoxicity of MTX-HYD and MTX and their analogues was determined by MTT cell proliferation assay kit, (Roche, Germany) as described earlier. Briefly, cells were seeded at the density of 25,000 cells/well in 96 well plate containing 100 µL of RPMI. Molecules at different concentration was added to the media and incubated in humidified CO$_2$ incubator. Untreated cells were taken as negative control and DMSO treated cells were taken as vehicle control. 48-hours post incubation, 10 µL of MTT (5 mg/mL) was added in each well in dark and incubated at 37° C. for the formation of formazan crystals. 4-hours post incubation, the crystals were dissolved using 100 µL isopropanol and the absorbance was read at 570 nm.

Example 4. Virus Isolates and Generation of Viral Stocks

Molecular clones for HIV-1$_{NL4.3}$, HIV-1$_{IIIB}$, HIV-1$_{ADA}$, HIV-1$_{89.6}$ virus isolates were obtained from NIH, AIDS Reagent Program, NIH, USA. HIV1$_{IndieC}$, which is a full length infectious molecular clone of Subtype C HIV-1 prevalent in India was a kind gift of Dr. M. Tatsumi, Japan. Virus stock was prepared by transfecting these molecular clones in HEK-293T cells using CalPhos Mammalian Transfection Kit (Clontech, USA). Briefly, 2.5×10$^6$ cells were seeded in 90 mm petri-dish and incubated at 37° C. for adherence. 12-hours post seeding, cells were transfected with various molecular clones independently according to manufacturer's protocol. 36-hours post transfection, supernatant was collected and virus was pelleted at 28,000 rpm at 4° C. for two and a half hours using ultracentrifuge in SW28 rotor. The pellet was suspended in serum free RPMI and used for infection.

Example 5. Determination of Infectivity

For infectivity of the prepared virus stocks, β-galactosidase staining assay was performed. For this, TZM-bl cells were infected with different concentrations of the virus prepared and incubated at 37° C. in humidified CO$_2$ incubator. 36-hours post incubation, cells were washed with 1×PBS and fixed with 0.5% Glutaraldehyde. Staining solution was added post fixation and blue stained cells were counted within 12 hours of staining.

Example 6. HIV-1 Infection and Anti-HIV Activity Assay

CEM-GFP, Jurkat J6, U937 and hPBMCs were infected with different isolates of HIV-1 as described previously. Briefly, cells were incubated with different isolates of HIV-1 in presence of polybrene (1 µg/mL) at 37° C. in humidified $CO_2$ incubator. 4-hours post incubation cells were washed with serum free RPMI and plated in complete RPMI. Cells were then treated with molecules at different concentrations. Untreated cells were taken as negative control and DMSO treated cells were taken as vehicle control. 72-hours post infection, supernatant was collected and virus production was determined by p24 antigen capture ELISA.

Example 7. p24 Antigen Capture ELISA

HIV-1 virus production was determined using p24 antigen capture ELISA kit (Advanced Bioscience Laboratories, USA) according to manufacturer's protocol. Briefly, 100 µL of viral particle containing supernatant was loaded in to the p24 primary antibody coated wells in presence of lysis buffer and incubated at 37° C. 1-hour post incubation, wells were washed using ELISA washer (Biorad, USA) and HRP-conjugate solution was added to the well and incubated at 37° C. for 1-hour. After incubation, wells were again washed and substrate solution was added and incubated at room temperature for 30 minutes to allow to blue colour to develop. The reaction was stopped using stop solution and absorbance was read at 450 nm using Molecular Devices M5 microplate reader. Percentage Inhibition of virus production was calculated using the following formula.

$$\% \ Inhibition = \frac{(p24 \ Conc. \ of \ untreated - p24 \ Conc. \ of \ treated)}{(p24 \ Conc. \ of \ untreated)} \times 100$$

Example 8. RNA Dependent DNA Polymerase Activity Assay of HIV-1 RT (RDDP Assay)

Effect of MTX-HYD and MTX on RNA dependent DNA polymerase activity of HIV-1 RT enzyme was tested with HIV-1 reverse transcriptase colorimetric assay kit (Roche, Germany) according to manufacturer's protocol. Briefly, 0.5 ng of recombinant HIV-1 reverse transcriptase enzyme in reaction buffer in presence or absence of MTX-HYD were incubated at room temperature for 5-10 min. Nevirapine (500 nM) treated wells were taken as positive control whereas untreated wells were taken as negative control and DMSO treated wells were taken as vehicle control. The reaction mixture containing Poly rA/OligodT (template/primers) and biotin or digoxigenin labelled dUTP nucleotide mixture was added to initiate the reverse transcription at 37° C. for 12-16 hours. After RT reaction, the mixture was loaded in to streptavidin-coated plates to allow binding of streptavidin with biotin in biotinylated nucleotides that were incorporated in newly synthesized DNA. Non-adhered nucleotides were removed by washing with wash buffer and anti-DIG-POD was added to allow the binding to digoxygenin nucleotides. ABTS substrate was then added to observe the colour reaction, which was read at 405 nm.

Example 9. Cell Free Assay for HIV-1 Integrase Activity

MTX-HYD was tested for its effect, if any, on HIV-1 Integrase enzyme using HIV-1 integrase assay kit (Xpress-Bio, USA) according to manufacturer's protocol. Briefly, biotin coated 5' Donor Strand (DS) was loaded on to streptavidin coated wells and incubated at 37° C. 30-minutes post incubation, wells were washed and unattached DS was removed. After washing, HIV-1 integrase enzyme and Transfer Strand (TS) were added to the wells in presence of MTX-HYD and incubated at 37° C. Raltegravir treated wells were taken as positive controls whereas untreated wells were taken as negative control and DMSO treated wells were taken as vehicle control. 30-minutes post incubation, wells were washed and 100 µL/well TMB substrate was added and incubated for 10-15 at room temperature. 100 µL/well TMB stop solution was added and absorbance was measured at 450 nm.

Example 10. Cell Free Assay for HIV-1 Protease Activity

Effect of MTX-HYD on HIV-1 Protease enzyme was determined using HIV-1 Protease Activity Assay Kit, Fluorometric (Biovision, USA) according to manufacturer's protocol. Briefly, in a single step reaction, HIV-1 protease enzyme was diluted in reaction buffer and 10 nmol/well was loaded in 96 well plate in presence or absence of MTX-HYD (100 nM). Indinavir (IND) (500 nM) treated wells were taken as positive control and untreated wells were considered as negative control. 15-minutes post addition, Fluorescence was measured using Molecular Devices M5 at Ex/Em=330/450 nm (FIG. 6).

Example 11. Screening of LOPAC$^{1280}$

TZM-bl cells were seeded at the density of 12,000-15,000 cells/well of 96 well plate with 100 µL DMEM (with 10% FBS) in each well. 12-hours post seeding, the media was replaced with fresh DMEM containing HTV-$1_{NLA.3}$ at 0.1 MOI and cells were treated with different molecules independently at 10 µM working concentration. Cells were incubated in humidified $CO_2$ incubator for 4-hours. After incubation, the media was replaced and cells were washed twice with incomplete DMEM and 100 µL of complete DMEM was added in each wells along with the molecules of interest and incubated at 37° C. in humidified $CO_2$ incubator. 48-hours post incubation, the media was removed and cells were washed twice with 100 µL of 1×PBS. After washing, cells were lysed using cell culture lysis reagent and Steady-Glo substrate was added at 1:1 ration in each well. Luminescence was measured using Molecular Devices M5 (Table 2). % Inhibition was calculated using following formula and plotted.

$$\% \ Inhibition = \frac{(RLU \ of \ untreated - RLU \ of \ treated)}{(RLU \ of \ untreated)} \times 100$$

(RLU=Relative Luminescence Unit)

Example 11. LOPAC$^{1280}$ Candidates Inhibit HIV-$1_{NLA.3}$ Virus Replication with Different Efficacy We further validated the anti-HIV activity of selected candidates in reporter T-cell line, CEM-GFP by determining their $IC_{50}$ (Inhibitory Concentration 50) values. These results indicate that LOPAC candidates inhibit HIV-1 replication with different efficacy at non-cytotoxic concentrations with $IC_{50}$ value ranging from 60 nM to 2.5 μM (FIG. 13).

Example 13 Statistical Analysis

All the statistical analysis was carried out by student's t-test using SigmaPlot 12.5. All the error bars in the graph represents Standard error of mean of at least three independent experiments. The significance of groups is designate as: ns=p>0.05, *=p<0.05, =p<0.01, *=p<0.001.

The invention claimed is:

1. A method of inhibiting a virus, comprising contacting a virus with methotrexate or an analogue of methotrexate (MTX), or methotrexate or an analogue of methotrexate in combination with one or more anti-viral agents,
wherein methotrexate is selected from methotrexate hydrate, methotrexate dihydrate and methotrexate tetrahydrate, and
wherein the analogue of methotrexate is selected from group consisting of MTX-methyl-d3-Dimethyl Ester, MTX Dimethyl Ester, MTX-methyl-d3, MTX heptaglutamate and MTX-d3 heptaglutamate.

2. The method of claim 1, wherein methotrexate and an analogue of methotrexate are used in combination with one or more anti-viral agent.

3. The method of claim 1, wherein the anti-viral agents are selected from group consisting of Tenofovir (TDF), Indinavir (IND), Raltegravir (RLT) and Maraviroc (MRV), Lamivudine (LMD), Nevirapine (NVP), Elvitegravir (ELVT) and Ritonavir (RTN).

4. The method of claim 1, wherein the inhibiting is performed in vitro on virus isolates selected from HIV-$1_{NL4.3}$, HIV-$1_{IndieC}$, HIV-$1_{IIIB}$, and HIV-$1_{ADA}$, HIV-$1_{89.6}$ with high efficiency.

5. The method of claim 1, wherein the inhibiting is performed in vivo in a subject infected with a virus, and wherein methotrexate and analogues of methotrexate are administered to the subject in a dose range of 0.01 mg/kg body weight to 100 mg/kg body weight.

6. A pharmaceutical composition comprising methotrexate or an analogue of methotrexate in combination with one or more anti-viral agents and a pharmaceutically acceptable excipient,
wherein methotrexate is selected from methotrexate hydrate, methotrexate dihydrate and methotrexate tetrahydrate, and
wherein the analogue of methotrexate is selected from group consisting of MTX-methyl-d3-Dimethyl Ester, MTX Dimethyl Ester, MTX-methyl-d3, MTX heptaglutamate and MTX-d3 heptaglutamate.

7. The pharmaceutical composition of claim 6, wherein the pharmaceutical composition is formulated for administration via oral, intradermal, transdermal, parenteral, intramuscular, intrathecal or suppository routes.

8. The method of claim 2, wherein the anti-viral agents are selected from group consisting of Tenofovir (TDF), Indinavir (IND), Raltegravir (RLT) and Maraviroc (MRV), Lamivudine (LMD), Nevirapine (NVP), Elvitegravir (ELVT) and Ritonavir (RTN).

9. The method of claim 5, wherein the dose range is 0.01 mg/kg body weight to 75 mg/kg body weight.

10. The method of claim 5, wherein the dose range is 0.01 mg/kg body weight to 50 mg/kg body weight.

* * * * *